United States Patent
Yamada et al.

(10) Patent No.: US 7,880,895 B2
(45) Date of Patent: Feb. 1, 2011

(54) OPTICAL TOMOGRAPHIC IMAGE PHOTOGRAPHING APPARATUS

(75) Inventors: Yoshiyuki Yamada, Toyokawa (JP); Yukihiro Higuchi, Gamagori (JP); Norimasa Satake, Nukata-gun (JP); Hisanari Torii, Gamagori (JP)

(73) Assignee: Nidek Co., Ltd., Gamagori-Shi (JP)

( * ) Notice: Subject to any disclaimer, the term of this patent is extended or adjusted under 35 U.S.C. 154(b) by 31 days.

(21) Appl. No.: 12/458,238

(22) Filed: Jul. 6, 2009

(65) Prior Publication Data

US 2010/0014089 A1   Jan. 21, 2010

(30) Foreign Application Priority Data

Jul. 4, 2008 (JP) .............................. 2008-176258

(51) Int. Cl.
*G01B 9/02* (2006.01)
*G01B 11/02* (2006.01)

(52) U.S. Cl. ........................................ 356/497; 356/479

(58) Field of Classification Search .................. 356/479, 356/497
See application file for complete search history.

(56) References Cited

U.S. PATENT DOCUMENTS

| | | | |
|---|---|---|---|
| 6,980,299 B1 | 12/2005 | de Boer | |
| 7,383,076 B2 * | 6/2008 | Ntziachristos et al. | 600/473 |
| 7,510,282 B2 | 3/2009 | Ueno et al. | |
| 7,527,378 B2 * | 5/2009 | Fukuma et al. | 351/205 |
| 7,557,928 B2 | 7/2009 | Ueno | |
| 2007/0046948 A1 * | 3/2007 | Podoleanu et al. | 356/497 |
| 2007/0188704 A1 * | 8/2007 | Fukuma et al. | 351/205 |
| 2007/0263208 A1 | 11/2007 | Yelin et al. | |
| 2008/0151256 A1 | 6/2008 | Kikawa et al. | |
| 2009/0237656 A1 * | 9/2009 | Ma | 356/300 |
| 2010/0007848 A1 * | 1/2010 | Murata | 351/206 |
| 2010/0014089 A1 * | 1/2010 | Yamada et al. | 356/450 |

FOREIGN PATENT DOCUMENTS

JP    A-2006-212153    8/2006

(Continued)

OTHER PUBLICATIONS

Oct. 28, 2009 search report issued in European Patent Application No. 09164546.5.

*Primary Examiner*—Patrick J Connolly
(74) *Attorney, Agent, or Firm*—Oliff & Berridge PLC

(57) ABSTRACT

An apparatus has an optical system detecting spectral information and having an optical scanner and a driving unit changing the optical path length by moving an optical member, a monitor, a control unit obtaining a tomographic image by performing Fourier analysis on the information and displaying the obtained image, and a unit previously setting an image on the monitor, in which the member is moved from an initial position and presence or absence of the tomographic image is determined, when the presence is detected, whether the tomographic image is normal or inverted is determined, and when the tomographic image is not the set image, the member is moved to obtain the set image, and when the tomographic image is the set image, the member is moved so that a position of the tomographic image in the depth direction coincides with a predetermined adjustment position and the driving unit is stopped.

5 Claims, 7 Drawing Sheets

FOREIGN PATENT DOCUMENTS

| | | |
|---|---|---|
| JP | A-2007-151622 | 6/2007 |
| JP | A-2008-501118 | 1/2008 |
| JP | A-2008-29467 | 2/2008 |
| WO | WO 2005/117534 A2 | 12/2005 |
| WO | WO 2008/039660 A2 | 4/2008 |

* cited by examiner

OPTICAL TOMOGRAPHIC IMAGE PHOTOGRAPHING APPARATUS

BACKGROUND OF THE INVENTION

1. Field of the Invention

The present invention relates to an optical tomographic image photographing apparatus arranged to photograph a tomographic image of an examined object.

2. Description of Related Art

Conventionally, as an optical tomographic image photographing apparatus arranged to photograph a tomographic image of an examined object, there is known an optical coherence tomograph (OCT) using low coherent light (see Japanese Patent Application Unexamined Publication No. 2006-212153). This apparatus is used for obtaining a tomographic image of a living body part such as an eyeball and a skin, for example.

In order for such an apparatus to obtain a tomographic image which is formed by interference light of measurement light projected onto the examined object and reference light, it is necessary to perform adjustment of the optical path length by moving an optical-path-length varying optical member (e.g., a reference mirror).

For example, in order for an apparatus arranged to photograph a tomographic image of a fundus of an examinee's eye to obtain a fundus tomographic image which is formed by interference light of measurement light projected onto the fundus and reference light, it is necessary to perform adjustment of the optical path length by moving an optical-path-length varying optical member (e.g., a reference mirror) corresponding to an eye axial length of the examinee's eye.

In a conventional technique of performing the above-described adjustment of the optical path length automatically, the reference mirror is moved from an initial position at which the optical path length of the reference light is shortest in a direction such that the optical path length is made longer, the presence or absence of the fundus tomographic image is determined at each moving position, and the reference mirror is moved based on a result of the determination.

When the fundus tomographic image is obtained by performing Fourier analysis on a detection signal obtained by photo-receiving the interference light, a normal image or an inverted image of the fundus tomographic image is obtained in accordance with the position of the reference mirror (sometimes no fundus tomographic image is obtained). In the technique described above, the reference mirror is moved from a position at which the optical path length of the reference light is shortest or a position at which the optical path length of the reference light is longest, by which a firstly obtained fundus tomographic image is previously set to be a normal image or an inverted image. For example, in the case of moving the reference mirror from the position at which the optical path length of the reference light is longest, the firstly obtained tomographic image is set to be the inverted image. Therefore, at the time when the presence of the fundus tomographic image is detected, the firstly obtained tomographic image is identified as the inverted image of the fundus tomographic image, and the reference mirror is moved from the position at which the inverted image is obtained in a direction such that the normal image is obtained, so that the normal image is displayed on a screen of a display monitor.

However, the technique described above requires long time to perform the adjustment of the optical path length because the optical-path-length varying optical member should be moved from the position at which the optical path length of the reference light is shortest or from the position at which the optical path length of the reference light is longest. In addition, a tomographic image desired by an examiner could not be displayed if the examinee's eye blinks when the optical-path-length varying optical member is located at a position at which the previously specified tomographic image (e.g., an inverted image) is obtained during the adjustment of the optical path length.

SUMMARY OF THE INVENTION

An object of the invention is to overcome the problems described above and to provide a fundus photographing apparatus which allows for smooth adjustment of the optical path length with respect to an examined object.

To achieve the objects and in accordance with the purpose of the present invention, an optical tomographic image photographing apparatus has an interference optical system arranged to detect spectral information from interference light of measurement light projected onto an examined object and reference light, and comprising an optical scanner arranged to scan the measurement light which is emitted from a light source on the examined object; and a driving unit arranged to change an optical path length by moving an optical member disposed in an optical path of one of the reference light and the measurement light in an optical axis direction, a monitor, a control unit arranged to control driving of the driving unit, and to obtain a tomographic image of the examined object by performing Fourier analysis on the spectral information and display the obtained tomographic image on a screen of the monitor, and an image setting unit arranged to previously set the tomographic image which is displayed on the screen of the monitor to be one of a normal image and an inverted image, wherein the control unit is arranged to control the driving of the driving unit so as to move the optical member from an initial position in a predetermined direction and determine presence or absence of the tomographic image on an image obtained at each position, when the presence of the tomographic image is detected, determine whether the tomographic image is the normal image or the inverted image, and when it is determined that the tomographic image is not the image previously set by the image setting unit, move the optical member in a direction such that the previously set image is obtained, and when it is determined that the tomographic image is the image previously set by the image setting unit, move the optical member so that a position of the tomographic image in the depth direction coincides with a predetermined adjustment position and then stop the driving of the driving unit.

Additional objects and advantages of the invention are set forth in the description which follows, are obvious from the description, or may be learned by practicing the invention. The objects and advantages of the invention may be realized and attained by the optical tomographic image photographing apparatus in the claims.

BRIEF DESCRIPTION OF THE DRAWINGS

The accompanying drawings, which are incorporated in and constitute a part of this specification, illustrate embodiments of the present invention and, together with the description, serve to explain the objects, advantages and principles of the invention. In the drawings.

DETAILED DESCRIPTION OF THE PREFERRED EMBODIMENTS

Figure 1:
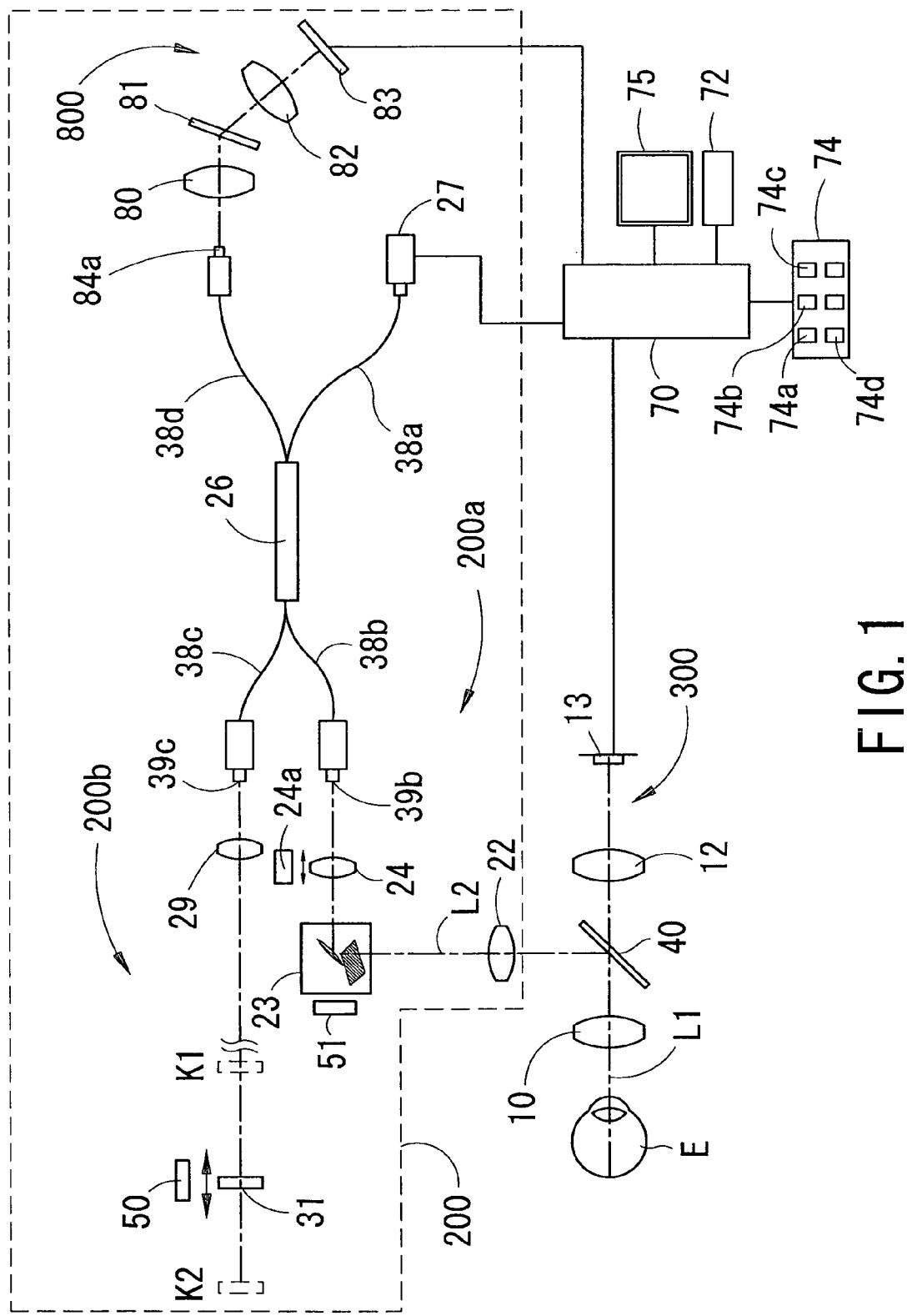
FIG. 1 is a view showing an optical system and a control system of an optical tomographic image photographing apparatus according to a preferred embodiment of the present invention.

A detailed description of one preferred embodiment of an optical tomographic image photographing apparatus embodied by the present invention is provided below with reference to the accompanying drawings. FIG. 1 is a view showing an optical system and a control system of the optical tomographic image photographing apparatus according to the present preferred embodiment of the present invention. In the descriptions provided below, a fundus photographing apparatus, which is one of ophthalmic photographing apparatuses, is taken as an example. Hereinafter, a depth direction of an examinee's eye E is referred to as a Z-direction (a direction of an optical axis L1), a horizontal direction on a plane which is perpendicular to the depth direction is referred to as an X-direction, and a vertical direction is referred to as a Y-direction.

In FIG. 1, the optical system is provided with an interference optical system (an OCT optical system) 200 and a fundus observation optical system 300. The interference optical system 200 is arranged to make a portion of low coherent light into measurement light, make another portion of the low coherent light into reference light, and combine the reference light and reflection light formed by the measurement light in order to make interference light. The fundus observation optical system 300 obtains a fundus image for fundus observation by photographing a fundus of the eye E illuminated with infrared light by using a two-dimensional photodetector. The interference optical system 200 includes a measurement optical system 200a and a reference light optical system 200b. In addition, the interference optical system 200 includes a spectral optical system 800 arranged to disperse the interference light of the reference light and the measurement light for each frequency (wavelength) and make the dispersed interference light photo-received by photo-receiving means (in the present preferred embodiment of the present invention, a one-dimensional photo-detector). A dichroic mirror 40 has properties of reflecting light having specific wavelength components that is used as the measurement light of the OCT optical system 200 and transmitting light having specific wavelength components that is used as the observation light of the fundus observation optical system 300.

First, a description of the OCT optical system 200 which is disposed at a reflection side of the dichroic mirror 40 is provided. An OCT light source 27 is arranged to emit low coherent light to be used as the measurement light and the reference light of the OCT optical system 200. An SLD light source is preferably used as the OCT light source 27. Specifically, a light source having a center wavelength of 840 nm and a bandwidth of 50 nm is used, for example. A fiber coupler 26 functions as both of a light dividing member and a light combining member. The light from the OCT light source 27 passes through an optical fiber 38a that functions as a light guide, and is divided into the reference light and the measurement light by the fiber coupler 26. The measurement light passes through an optical fiber 38b and heads for the eye E. The reference light passes through an optical fiber 38c and heads for a reference mirror 31.

On an optical path where the measurement light travels to the eye E, an end portion 39b of the optical fiber 38b from which the measurement light exits, a focusing lens 24 which is movable in an optical axis direction in accordance with refractive error of the eye E, a scanning unit 23 which is defined by a combination of two galvano mirrors capable of scanning the measurement light in the X- and Y-directions on the fundus by driving of a scanning driving mechanism 51, and a relay lens 22 are disposed. The dichroic mirror 40 and an objective lens 10 function as a light guiding optical system arranged to guide the OCT measurement light from the OCT optical system 200 to the fundus.

The measurement light reflected from the fundus passes through the objective lens 10, is reflected by the dichroic mirror 40, and heads for the OCT optical system 200, where the measurement light enters the end portion 39b of the optical fiber 38b via the relay lens 22, the two galvano mirrors of the scanning unit 23, and the focusing lens 24. The measurement light which enters the end portion 39b reaches an end portion 84a of an optical fiber 38d via the optical fiber 38b, the fiber coupler 26, and the optical fiber 38d.

On an optical path where the reference light travels to the reference mirror 31, an end portion 39c of the optical fiber 38c from which the reference light exits, a collimator lens 29, and the reference mirror 31 are disposed. The reference mirror 31 is movable in an optical axis direction by a reference-mirror driving mechanism 50 in order to change the optical path length of the reference light.

The reference light which is thus formed from the light emitted from the OCT light source 27, and the reflection light from the fundus which is formed from the measurement light with which the fundus is illuminated are combined by the fiber coupler 26 to be made into the interference light. Then, after passing through the optical fiber 38d, the interference light exits from the end portion 84a. The spectral optical system (a spectrometer unit) 800 arranged to disperse the interference light into frequency components in order to obtain an interference signal for each of the frequencies includes a collimator lens 80, a grating mirror (a diffraction grating) 81, a condenser lens 82, and a photodetector 83. For the photodetector 83, a one-dimensional detector (a line sensor) which has sensitivity to an infrared range is used.

To be specific, the interference light exiting from the end portion 84a is made into parallel light by the collimator lens 80, and then is dispersed into the frequency components by the grating mirror 81. The interference light dispersed into the frequency components is collected on a photo-receiving surface of the photodetector 83 via the condenser lens 82. Thus, spectral information on interference fringes is recorded at the photodetector 83. Then, the spectral information is inputted into a control unit 70, and is analyzed by performing Fourier transform thereon, whereby information in the depth direction of the eye E can be obtained. At this time, the control unit 70 can obtain a tomographic image by controlling the scanning unit 23 to scan the measurement light in a predetermined traverse direction on the fundus. For example, scanning the measurement light in the X- or Y-direction allows a tomographic image on an X-Z or Y-Z plane of the fundus to be obtained (in the present preferred embodiment of the present invention, a mode of thus obtaining the tomographic image by one-dimensionally scanning the measurement light on the fundus is referred to as B-scan). The obtained tomographic image is stored in a memory 72 connected to the control unit 70. It is also possible to obtain a three-dimensional image of the fundus by two-dimensionally scanning the measurement light in the X- and Y-directions.

To be specific, the control unit 70 obtains spectral intensity of the interference light based on a photo-receiving signal outputted from the photodetector 83, and rewrites the spectral intensity to a function of a wavelength λ by using a correspondence relation between the positions of pixels of the photodetector 83 which are previously stored in the memory 72 and the wavelength λ. Then, the spectral intensity I(λ) is converted into a function I(k) which is equidistant with reference to a wave number k (=2π/λ).

Next, a description of dispersion correction processing is provided. It should be noted that the effects of dispersion include shifting a phase of an interference component, lowering a peak of a multiplexed signal of each wavelength, and broadening a signal (lowering resolution).

Hence, in the dispersion correction processing, the phase subjected to the shifting is converted back for each wavelength in order to correct the lowering of the resolution due to the lowering of the interference signal. To be specific, a phase shift φ(k) as a function of the wave number k is previously obtained, and the shifting of the phase is converted back for each k value by using $I(k) \cdot exp^{-i\phi(k)}$. The phase shift φ(k) to be subjected to the dispersion correction processing may be obtained previously by calibration, or the phase shift φ(k) corresponding to the obtained tomographic image may be obtained. For the details of the technique of performing the dispersion correction processing by using software as described above, please refer to U.S. Pat. No. 6,980,299 and Published Japanese Translation No. 2008-501118 of the PCT International Publication, for example.

In the case of previously obtaining data on the dispersion correction processing by calibration, for example, adjustment of the optical path length of the reference light is performed by moving the reference mirror 31, and first dispersion correction data (a phase shift $\phi 1(k)$) which is calculated based on a fundus tomographic image being a normal image (visibility on the retinal surface side is higher) and second dispersion correction data (a phase shift $\phi 2(k)$) which is calculated based on a fundus tomographic image being an inverted image (visibility on the choroidal side is higher) are previously calculated and stored in the memory 72. Accordingly, the first dispersion correction data for performing dispersion correction processing on the normal image and the second dispersion correction data for performing dispersion correction processing on the inverted image are prepared.

Then, the control unit 70 obtains the information in the depth direction of the eye E by performing Fourier transform on the spectral intensity I(k) which has been subjected to the dispersion correction processing by using the previously set dispersion correction data.

In the case of using the dispersion correction data corresponding to the obtained tomographic image, the first dispersion correction data (the phase shift $\phi 1(k)$) is calculated in real time based on the fundus tomographic image being a normal image. Then, the spectral intensity I(k) which has been corrected by the first dispersion correction data is subjected to Fourier transform so as to obtain the information in the depth direction. In addition, the second dispersion correction data (the phase shift $\phi 2(k)$) is calculated in real time based on the fundus tomographic image being an inverted image. Then, the spectral intensity I(k) which has been corrected by the second dispersion correction data is subjected to Fourier transform so as to obtain the information in the depth direction. Even if the optical member for the dispersion correction processing is placed in one of the optical path of the reference light and the optical path of the measurement light, the dispersion correction processing described above can be performed to reverse the effects of the dispersion correction processing.

Next, a description of the fundus observation optical system 300 is provided. The fundus observation optical system 300 is provided with the objective lens 10, an image-pickup lens 12, and a two-dimensional image-pickup element 13. The light reflected from the fundus illuminated by an illumination optical system for fundus observation (not shown) passes through the objective lens 10, the dichroic mirror 40, and the image-pickup lens 12, and forms an image on the image-pickup element 13. An image-pickup signal outputted from the image-pickup element 13 is inputted into the control unit 70. The control unit 70 displays a fundus image picked up by the image-pickup element 13 on a screen of a display monitor 75. The fundus image picked up by the image-pickup element 13 is used for fundus observation and for alignment with the eye E at the time when the fundus tomographic image is obtained.

The control unit 70 is connected with the monitor 75, the memory 72, a control section 74, the driving mechanism 50, a driving mechanism 24a arranged to move the focusing lens 24 in the optical axis direction, and other constituent elements. The control section 74 is provided with a measurement starting switch 74a, a measurement position setting switch 74b, an auto coherence switch 74c, and a mode changing switch 74d. When the auto coherence switch 74c is pressed, a trigger signal for starting the adjustment of the optical path length corresponding to an eye axial length of the eye E is inputted to the control unit 70.

Figure 2:
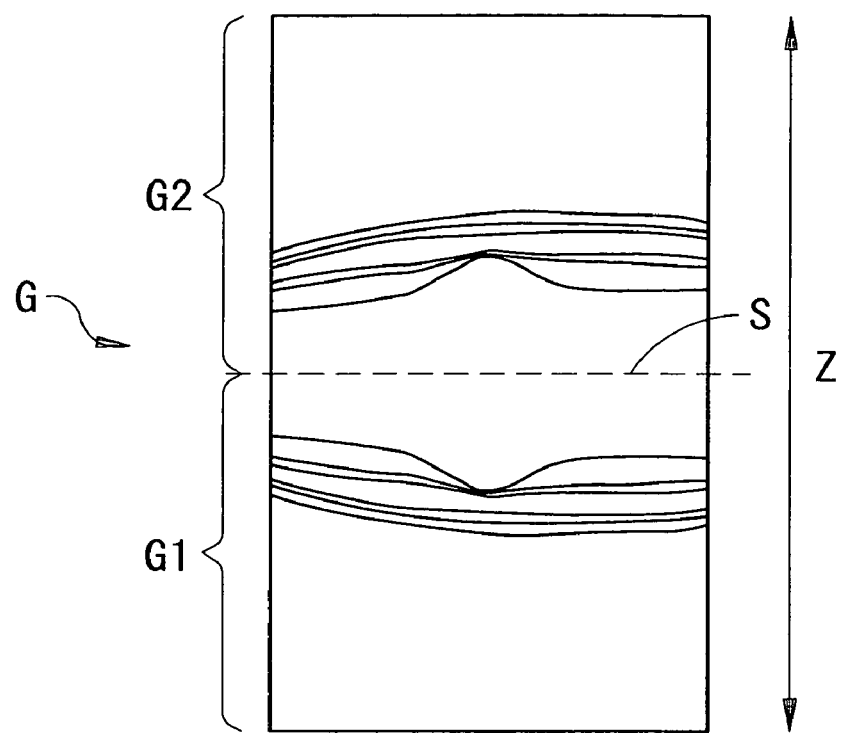
FIG. 2 is a view showing an example of a tomographic image obtained by an OCT optical system.

FIG. 2 is a view showing an example of the tomographic image obtained (formed) by the OCT optical system 200. Image data G consists of first image data G1 and second image data G2 which is a mirror image of the first image data G1, and the first and second image data G1 and G2 are symmetric with respect to a depth position S at which the optical path length of the measurement light and the optical path length of the reference light become equal. The control unit 70 extracts one of the first image data G1 and the second image data G2 in the image data G and displays the extracted one on the screen of the monitor 75. In the present preferred embodiment of the present invention, the first image data G1 is extracted. In the fundus tomographic image obtained by the interference optical system 200 based on the principle of Fourier domain OCT, visibility (interference visibility) is highest at the depth position at which the optical path length of the measurement light and the optical path length of the reference light become equal (a depth position corresponding to the location of the reference mirror 31) and is lowered with distance from the depth position. Therefore, an image with high visibility and high resolution is obtained in a fundus portion close to the depth position, while an image with less visibility and less resolution is obtained in a portion distant from the depth position.

Hence, the apparatus has such a configuration that a photographing mode according to an observed portion is selectable in order that a fundus portion desired by an examiner can be observed with high visibility and high resolution. To be specific, the photographing mode is previously selectable between a retinal mode of displaying a retinal surface side portion with high visibility (a first mode for observing the front side of the fundus) and a choroidal mode of displaying a choroidal side portion with high visibility (a second mode for observing the back side of the fundus). The mode changing switch 74*d* for selecting either of the modes is provided to the control section 74. The control unit 70 controls the movement of the reference mirror 31 in response to a mode selection signal inputted from the mode changing switch 74*d*.

When the reference mirror 31 is located such that the depth position at which the optical path length of the measurement light and the optical path length of the reference light become equal is positioned on the front side of the retinal surface, a fundus tomographic image whose visibility is higher on the retinal surface side and lower on the choroidal side (i.e., a normal image) is obtained. In this case, the first image data G1 and the second image data G2 which is a mirror image of the first image data G1 face each other. On the other hand, when the reference mirror 31 is located such that the depth position at which the optical path length of the measurement light and the optical path length of the reference light become equal is positioned on the back side of the retinal surface, a fundus tomographic image whose visibility is higher on the choroidal side and lower on the retinal surface side (i.e., an inverted image) is obtained. In this case, the first image data G1 and the second image data G2 which is a mirror image of the first image data G1 face opposite directions from each other.

When a selection signal of the retinal mode is inputted from the mode changing switch 74*d*, the control unit 70 reads out the first dispersion correction data (for a normal image) as a dispersion correction value for correcting the effects of the dispersion from the memory 75, corrects data on the spectral intensity outputted from the photodetector 83 by using the first dispersion correction data, and generates tomographic image data by performing Fourier transform on the corrected spectral intensity data. Accordingly, the normal image of the fundus tomographic image is obtained with high visibility and high resolution, and the inverted image of the fundus tomographic image is obtained with blur and low resolution due to the difference in the dispersion correction data.

When a selection signal of the choroidal mode is inputted from the mode changing switch 74*d*, the control unit 70 reads out the second dispersion correction data (for an inverted image) as a dispersion correction value for correcting the effects of the dispersion from the memory 75, corrects data on the spectral intensity outputted from the photodetector 83 by using the second dispersion correction value, and generates tomographic image data by performing Fourier transform on the corrected spectral intensity data. Accordingly, the inverted image of the fundus tomographic image is obtained with high visibility and high resolution, and the normal image of the fundus tomographic image is obtained with blur and low resolution due to the difference in the dispersion correction data.

The descriptions provided below refer to the first image data G1 in which the fundus tomographic image whose visibility is higher on the front surface side of the fundus than the choroidal side is identified as the normal image, and the fundus tomographic image whose visibility is higher on the choroidal side than the front surface side of the fundus is identified as the inverted image.

Descriptions of operations of the apparatus having the configuration described above are provided. First, the examiner performs alignment in order to bring a measurement optical axis to the pupil center on an image photographed by a camera for anterior-segment observation (not shown), and then makes the examinee to fixate a movable fixation lamp (not shown) so that a desired portion is measured. In addition, the examiner selects an observation mode of the fundus tomographic image by using the mode changing switch 74*d*. The following descriptions are provided based on a situation in which the retinal mode is selected.

Figure 3:
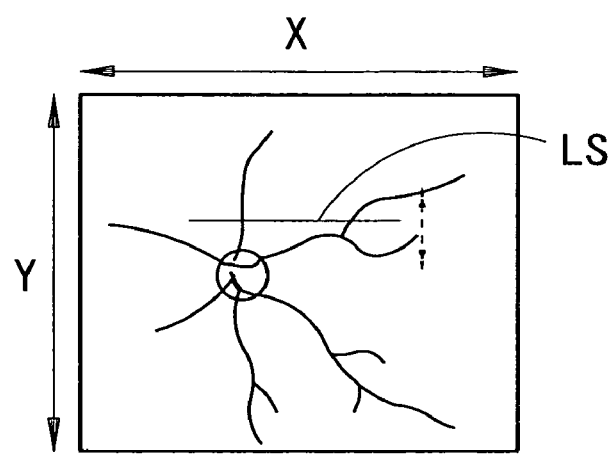
FIG. 3 is a view showing a fundus observation image obtained by a fundus observation optical system on a screen of a display monitor.

FIG. 3 is a view showing the fundus observation image obtained by the fundus observation optical system 300 on the screen of the monitor 75. The examiner performs focusing on the fundus based on the infrared fundus image on the monitor 75, and then presses the auto coherence switch 74*c*. The control unit 70 controls driving of the driving mechanism 50 based on an operation signal inputted from the auto coherence switch 74*c* to move the reference mirror 31 and perform adjustment of the optical path length of the reference light in order to obtain the normal image of the fundus tomographic image. In this operation, the control unit 70 moves the reference mirror 31 from a set initial position in one direction in given steps, determines whether a firstly obtained tomographic image is the normal image or the inverted image by image processing, and controls a direction of subsequent movement of the reference mirror 31 based on a result of the determination and the set observation mode.

A movable range of the reference mirror 31, which is moved in the optical axis direction by the driving of the driving mechanism 50, is set so as to correspond to eye axial lengths of different examinee's eyes. In FIG. 1, the reference mirror 31 is movable in a range between a movement limiting position K1 in a direction such that the optical path length of the reference light is made shorter and a movement limiting position K2 in a direction such that the optical path length of the reference light is made longer.

The initial position (a movement start position) of the reference mirror 31 during the automatic adjustment of the optical path length is set at some midpoint in the movable range of the reference mirror 31 corresponding to the eye axial length of the examinee's eye (i.e., a position such that the optical path length of the reference light can be made longer and shorter), and is preferably set in the vicinity of a position in response to the examinee's eye having an average eye axial length (e.g., 24 mm). In the present preferred embodiment of the present invention, the initial position is set at a position corresponding to an eye axial length (20 mm) which is slightly shorter than the average eye axial length (24 mm). Accordingly, the normal image of the fundus tomographic image is obtained when the tomographic image of the examinee's eye having the eye axial length of 20 mm is obtained with the reference mirror 31 being located at the initial position.

After the control unit 70 obtains the tomographic image at the previously set initial position, the control unit 70 moves the reference mirror 31 in given steps in the direction such that the optical path length of the reference light is made longer (a direction such that the difference between the optical path length of the reference light and the optical path length of the measurement light is made shorter) while sequentially obtaining a tomographic image at each moving position, in order to search for a position at which a fundus tomographic image is obtained. At this time, each time the reference mirror 31 is stopped at each discretely distributed moving position, the control unit 70 analyzes the tomographic image obtained at the position, and performs determination of the presence or absence of the fundus tomographic image, determination whether the fundus tomographic image is the normal image or the inverted image, and detection of an image position. As for the step for moving the reference mirror 31, if a photographing range Z1 in the depth direction of the first image data G1 for the normal image is 2 mm, the reference mirror 31 is moved so that a photographing region on the fundus is moved in about 2 mm steps.

Figure 4:
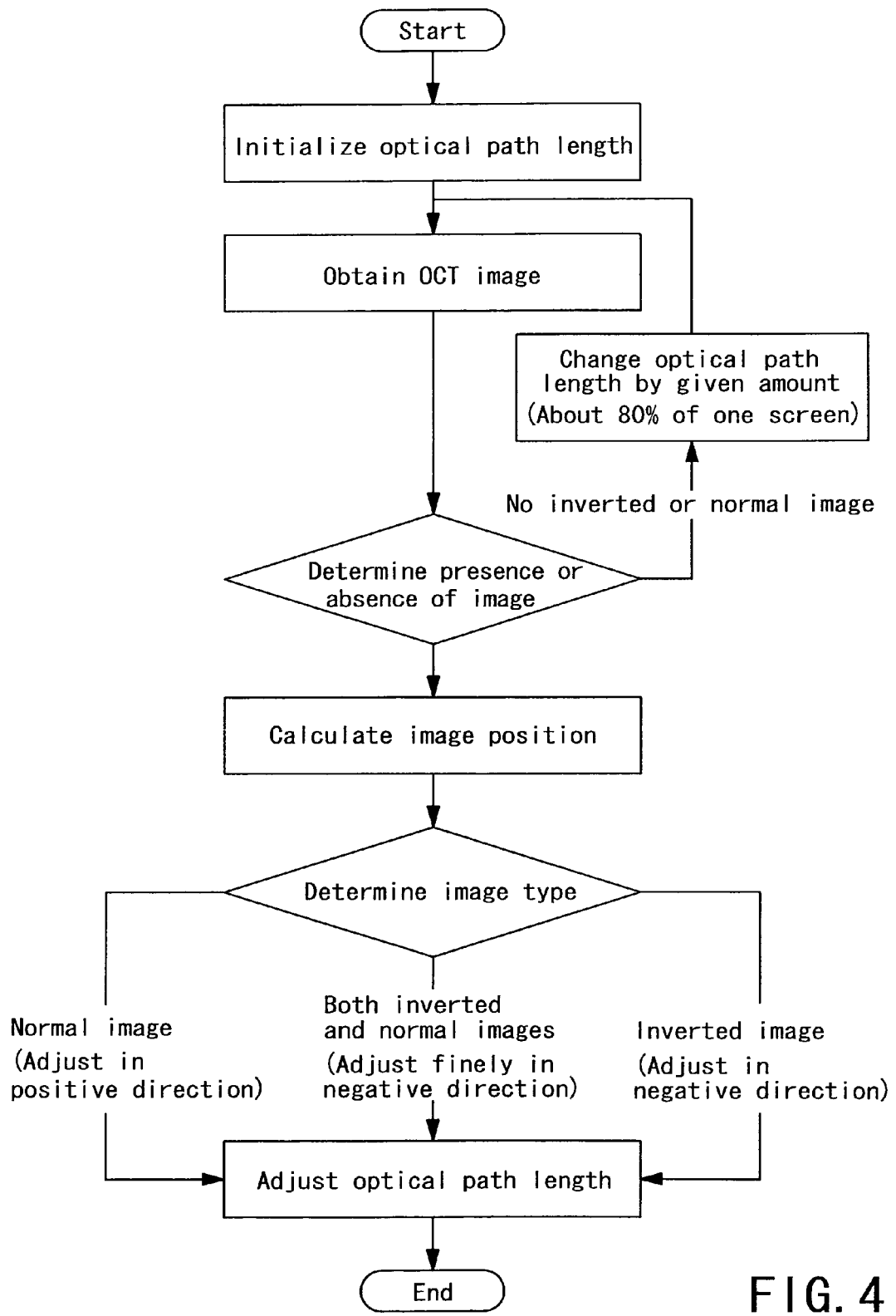
FIG. 4 is a flow chart showing an example of analyzing the obtained tomographic image by image processing.

Hereinafter, a description of an example of analyzing the obtained tomographic image by image processing will be provided referring to a flow chart shown in FIG. 4.

Figure 5:
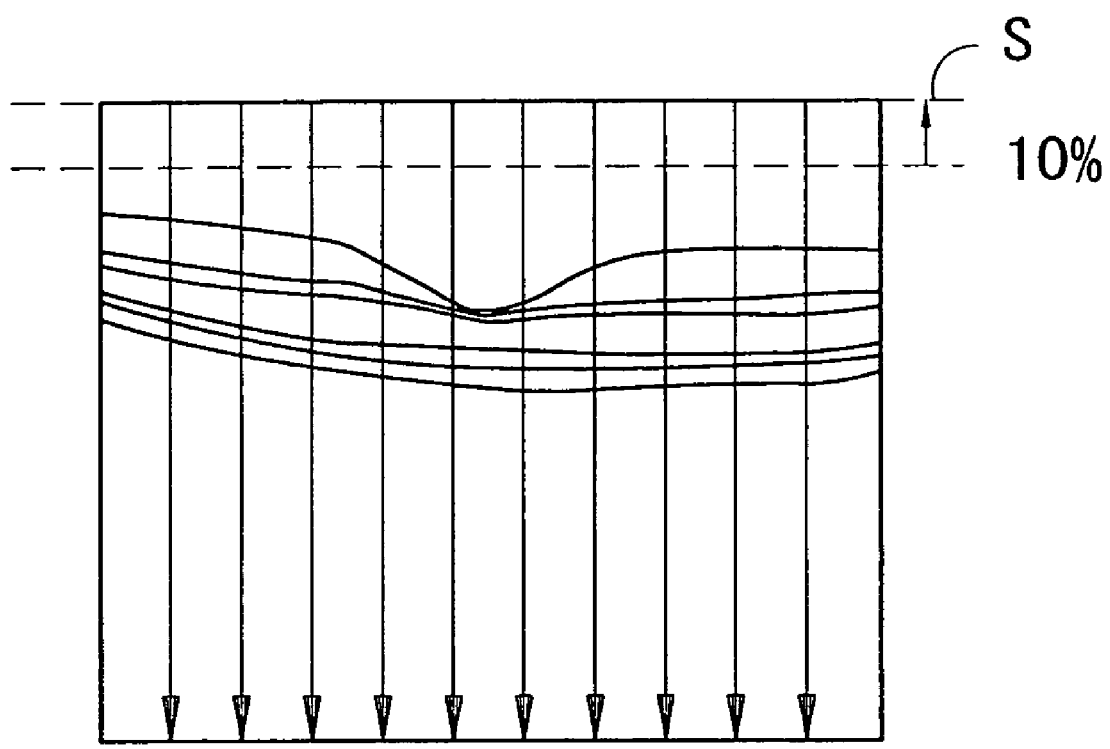
FIG. 5 is a view for explaining scanning lines scanned on the tomographic image for obtaining luminance distribution data on the tomographic image.

First, the control unit 70 sets a plurality of scanning lines for scanning in the depth direction on the tomographic image (a direction of A-scan) as shown in FIG. 5, and obtains luminance distribution data on each scanning line. In FIG. 5, the tomographic image is split into eleven, and the scanning lines are defined by ten splitting lines. In order to remove the influence of noise generated on the upper portion of the tomographic image, data in the vicinity of the upper end of the tomographic image (e.g., 10% of the tomographic image in the upper portion) is not subjected to image processing. In addition, in order to avoid the influence of noise, smoothing is performed in such a manner that the average value of values at five points on the right and left sides of the scanning line is regarded as data of the scanning line. In addition, in order to emphasize a sharp rising edge of a normal image, the control unit 70 extracts data at one point out of every three points in the depth direction (thinning).

Figure 6:
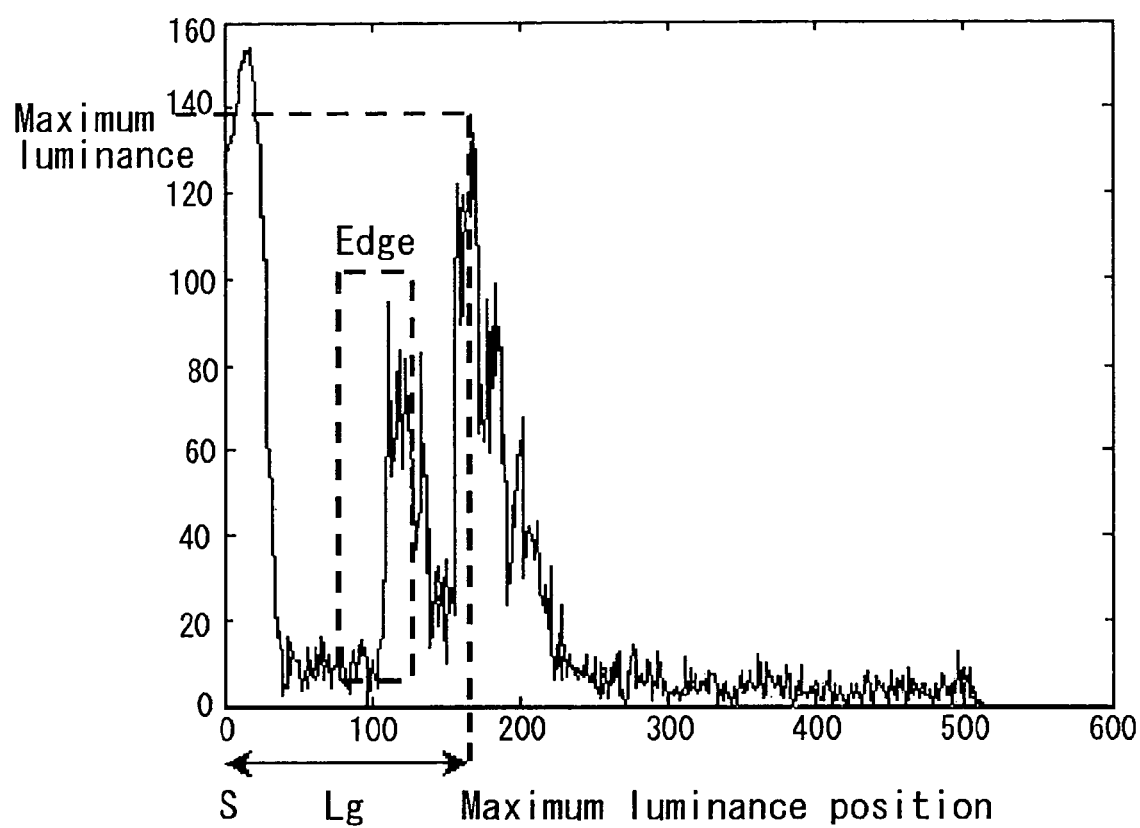
FIG. 6 is a graph showing a variation of luminance distribution in a depth direction of a fundus tomographic image.

FIG. 6 is a view showing a variation of the luminance distribution in the depth direction of the fundus tomographic image. The control unit 70 calculates the maximum luminance value in the luminance distribution of each scanning line, calculates the detected position of the maximum luminance value in the depth direction, and determines the presence or absence of the fundus tomographic image in the whole tomographic image based on a result of the calculation for each scanning line. The control unit 70 calculates the average value of the maximum luminance values of the respective scanning lines and detects the presence of the fundus tomographic image if the calculated average value is equal to or greater than a predetermined threshold value (e.g., equal to or greater than 35 where the luminance value is indicated by 256 levels), and determines the absence of the fundus tomographic image if the calculated average value is smaller than the predetermined threshold value (e.g., smaller than 35 where the luminance value is indicated by 256 levels).

When no fundus tomographic image is detected in the tomographic image obtained when the reference mirror 31 is in the initial position, the control unit 70 moves the reference mirror 31 to the next previously set moving position and determines the presence or absence of the fundus tomographic image based on the tomographic image which is obtained at the moving position. In this way, the control unit 70 moves the reference mirror 31 in predetermined steps until the presence of the fundus tomographic image is detected. If no fundus tomographic image is detected even though the reference mirror 31 reaches the movement limiting position K2, the control unit 70 returns the reference mirror 31 to the initial position and moves the reference mirror 31 in the direction such that the optical path length of the reference light is made shorter in predetermined steps until the presence of the fundus tomographic image is detected (the first tomographic image is obtained).

Figure 8A:
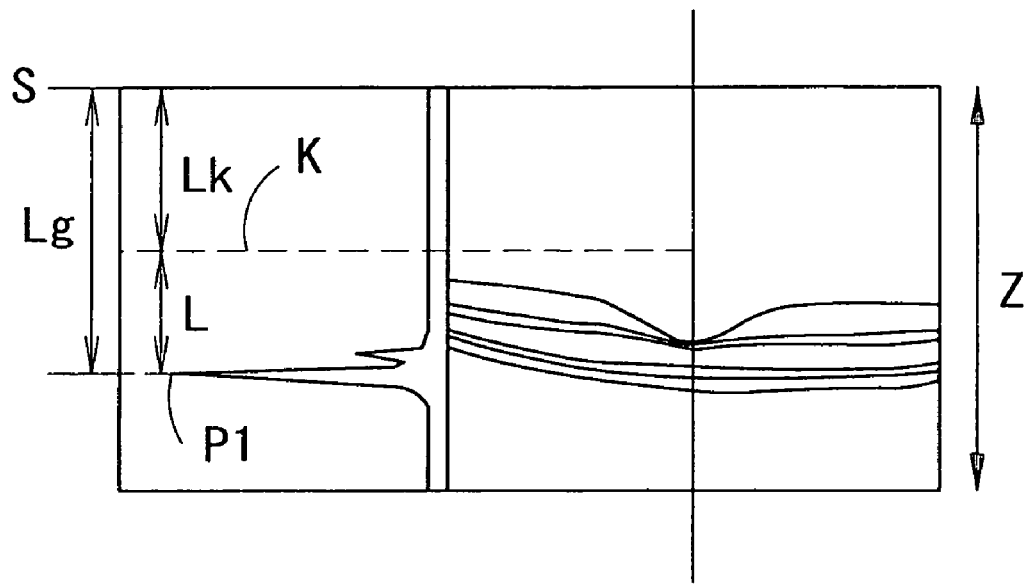
FIGS. 8A and 8B are views for explaining a control operation when the tomographic image is to be displayed at a predetermined display position.
Figure 8B:
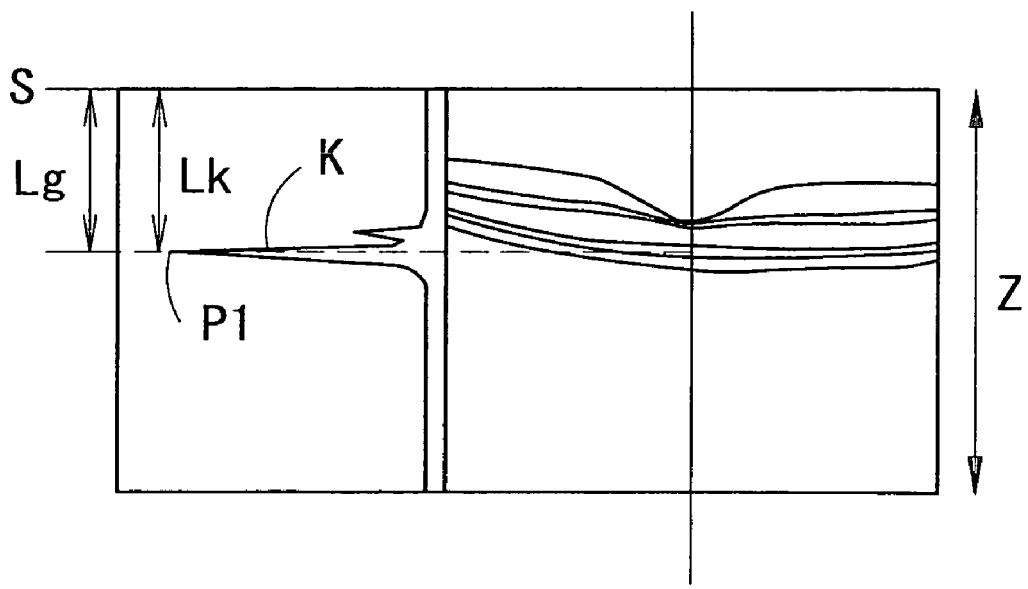

When the presence of the fundus tomographic image in the obtained tomographic image is detected, the control unit 70 detects the average position of the detected positions of the maximum luminance values in the respective scanning lines calculated as described above as an image position P1 of the fundus tomographic image. Then, the control unit 70 calculates a deviation amount Lg from the depth position S at which the optical path length of the measurement light and the optical path length of the reference light become equal (the upper end position of the first image data G1) to the image position P1. In other words, the control unit 70 detects the image position of the fundus tomographic image with respect to the depth position S at which the optical path length of the measurement light and the optical path length of the reference light become equal (see FIG. 8).

The control unit 70 determines that the normal image and the inverted image of the fundus tomographic image are coexistent if the image position P1 of the fundus tomographic image calculated as described above is located in the vicinity of the upper end of the tomographic image (e.g., in a region corresponding to one fourth of the tomographic image in the upper portion). In such a case, the control unit 70 moves the reference mirror 31 by a predetermined amount in a direction such that only the normal image is obtained (the direction such that the optical path length of the reference light is made shorter). It is preferable that a movement direction and a movement amount of the reference mirror 31, which are required for bringing the state that the normal image and the inverted image are coexistent to a state that only the normal image is obtained, are previously calculated by experiment or simulation, and the movement direction and amount are previously stored in the memory 72.

If the image position P1 of the fundus tomographic image calculated as described above is not located in the vicinity of the upper end of the image, the control unit 70 determines that only one of the normal image and the inverted image of the fundus tomographic image is present in the tomographic image. In this case, the control unit 70 determines whether the tomographic image is the normal image or the inverted image for each scanning line based on the luminance distribution calculated as described above.

Figure 7A:
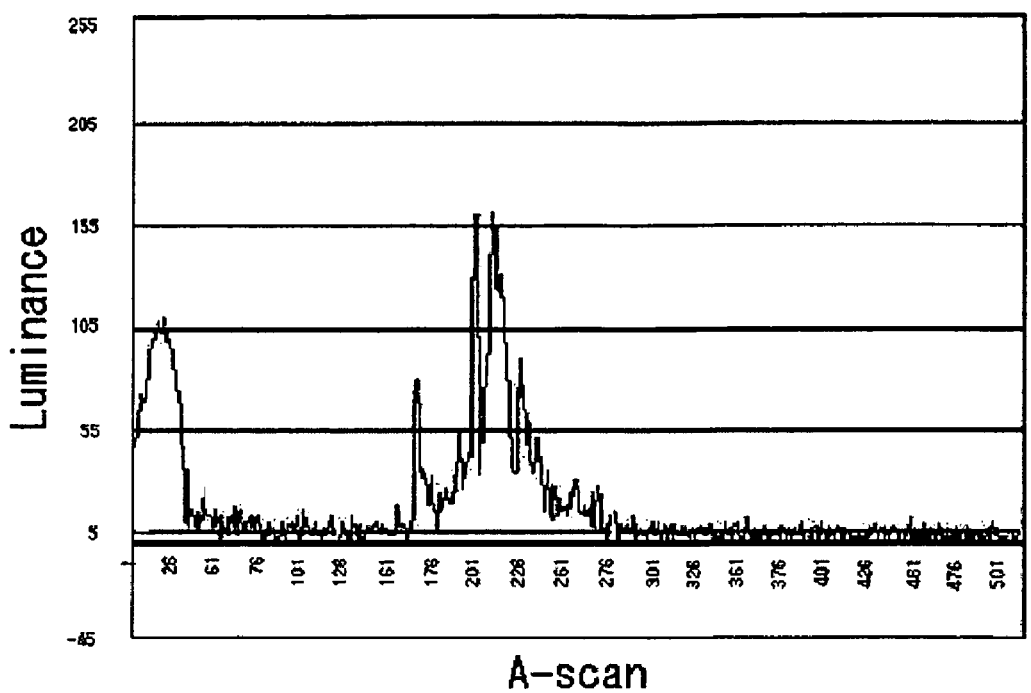
FIGS. 7A and 7B are graphs showing examples of the luminance distribution data on each scanning line.
Figure 7B:
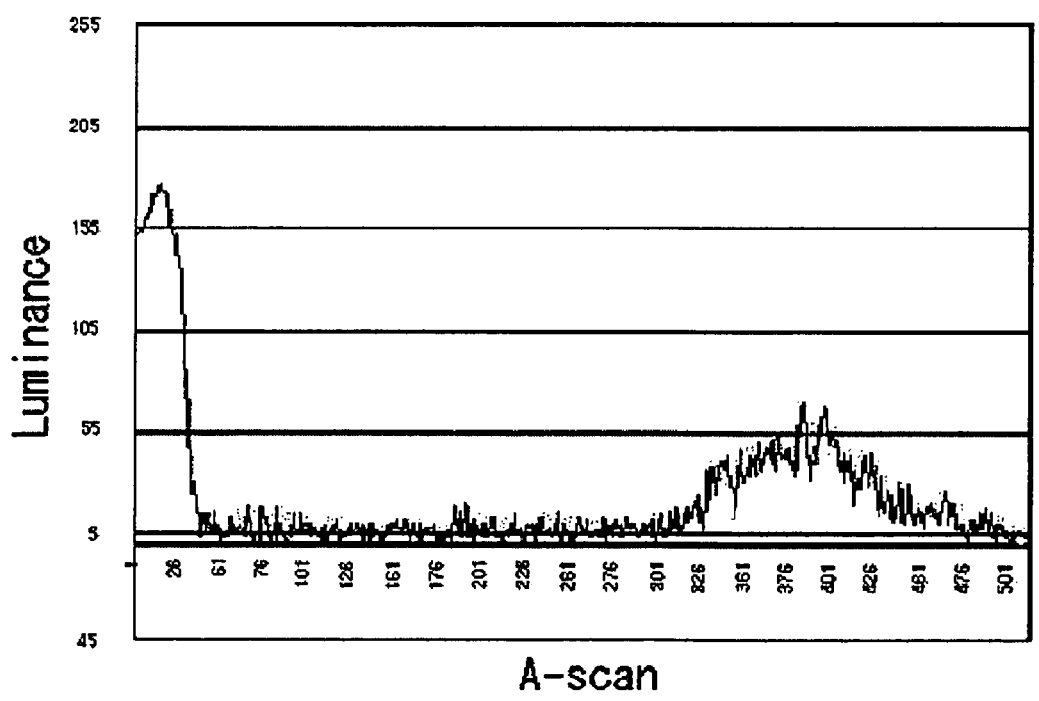

FIGS. 7A and 7B are views showing examples of the luminance distribution data on each scanning line. FIG. 7A is a view showing the luminance distribution when the normal image is obtained, and FIG. 7B is a view showing the luminance distribution when the inverted image is obtained. As shown in FIGS. 7A and 7B, the rising of the luminance is steep in the normal image, and the rising of the luminance is gentle in the inverted image. In other words, the normal image and the inverted image are different in the variation of the luminance value (the edge) toward a high luminance portion (a portion corresponding to the fundus tomographic image).

Hence, the control unit 70 calculates an amount of the variation of the luminance value (a rising degree of the edge) from the luminance distribution for each scanning line, and determines whether the tomographic image is the normal image or the inverted image for each scanning line based on a result of the calculation. The control unit 70 counts the number of scanning lines whose amount of the variation (inclination) of the edge being the variation of the luminance exceeds a predetermined threshold value. The control unit 70 determines that the fundus tomographic image is the normal image if the number is one or more and determines that the fundus tomographic image is the inverted image if the number is zero. The variation amount of the edge is obtained by sampling difference values of the luminance values at adjacent depth positions by using the luminance values at the respective depth positions which are extracted by thinning.

Then, the control unit 70 determines whether the fundus tomographic image is the normal image or the inverted image as the whole tomographic image based on the determination results on whether the fundus tomographic image is the normal image or the inverted image for the respective scanning lines. If it is determined that the fundus tomographic image is the normal image in three or more scanning lines among ten scanning lines, the control unit 70 determines that the fundus tomographic image is the normal image, and if it is determined that the fundus tomographic image is the normal image in two or less scanning lines among ten scanning lines, the control unit 70 determines that the fundus tomographic image is the inverted image.

If it is determined that the obtained fundus tomographic image is the inverted image, the control unit 70 moves the reference mirror 31 in the direction such that the normal image is obtained (the direction such that the reference light is made shorter). At this time, the control unit 70 calculates a movement amount ML of the reference mirror 31 by which the deviation amount Lg calculated as described above becomes zero, and moves the reference mirror 31 by double the calculated movement amount ML. Accordingly, only the normal image is obtained. In this case, it is preferable that a variation amount of the deviation amount Lg when the reference mirror 31 is moved by a given amount is previously calculated. Accordingly, the control unit 70 is allowed to move the reference mirror 31 so that the deviation amount Lg from the depth position S to the image position P1 becomes the predetermined deviation amount and display the fundus tomographic image at a given display position.

If it is determined that the obtained fundus tomographic image is the normal image, the control unit 70 moves the reference mirror 31 so that the image position of the tomographic image in the depth direction coincides with a predetermined adjustment position, and then stops moving the reference mirror 31.

To be specific, the control unit 70 regards the detected position of the maximum luminance value in the depth direction of the normal image as the image position P1, calculates a deviation amount L in the depth direction between a predetermined optical path length adjustment position K (see broken lines in FIGS. 8A and 8B) and the image position P1, moves the reference mirror 31 so that the deviation amount L becomes zero, and then stops moving the reference mirror 31. Accordingly, the fundus tomographic image is displayed at a desired display position on the monitor 75. The optical path length adjustment position K is defined by a deviation amount Lk between the depth position S at which the optical path length of the measurement light and the optical path length of the reference light become equal (the upper end of the first image data G1) and the optical path length adjustment position K. The control unit 70 obtains the difference between the deviation amount Lk and the deviation amount Lg in the depth direction as the deviation amount L.

If it is determined that the fundus tomographic image is the inverted image as described above or that the normal image and the inverted image of the fundus tomographic image coexist, the control unit 70 moves the reference mirror 31 in the direction such that the normal image is obtained (the direction such that the reference light is made shorter) as described above, and when only the normal image is obtained, the control unit 70 calculates the deviation amount L between the predetermined optical path length adjustment position K (see the dashed lines K in FIGS. 8A and 8B) and the image position P1 and moves the reference mirror 31 so that the deviation amount L becomes zero.

When the reference mirror 31 is moved to the position at which the normal image of the fundus tomographic image is obtained and the normal image is obtained by the interference optical system 200, the control unit 70 displays the normal image of the fundus tomographic image at a predetermined display position on the monitor 75. Because the tomographic image thus obtained has passed through the correction processing using the first dispersion correction data for normal image obtainment, a normal image of a fundus tomographic image with high contrast and high definition is displayed on the monitor 75. Accordingly, the examiner is allowed to observe an area of the retina of the examinee's eye with high visibility.

When displaying the fundus tomographic image on the screen of the monitor 75, the control unit 70 controls display of the monitor 75 so that the retinal surface portion is displayed on the upper side of the screen of the monitor 75. When the selection signal of the retinal mode is inputted, the control unit 70 displays the extracted first image data G1 without performing inversion thereon.

Owing to the configuration described above, even if the reference mirror 31 is moved from some midpoint in its movable range, whether the obtained fundus tomographic image is the normal image or the inverted image can be determined by image processing, and the adjustment of the optical path length before obtaining a desired OCT image can be performed in a short time. Thus, the examiner can smoothly start observation of the tomographic image. In addition, the burden on the examinee can be reduced.

In addition, because whether the obtained fundus tomographic image is the normal image or the inverted image can be determined by image processing, even if the examinee's eye blinks during the adjustment of the optical path length, a tomographic image desired by the examiner can be smoothly obtained.

In the descriptions provided above, the difference between the optical path length of the measurement light and the optical path length of the reference light is adjusted by changing the optical path length of the reference light by moving the reference mirror 31 defining an optical path length variable member. However, the collimator lens 29 and the fiber end 39c may be integrally moved (see Japanese Patent Application Unexamined Publication No. 2007-151622).

In addition, the difference between the optical path length of the measurement light and the optical path length of the reference light may be adjusted by changing the optical path length of the measurement light. For example, in the optical system in FIG. 1, the reference mirror 31 is fixed and the relay lens 24 and the fiber end 39b are integrally moved, so that the optical path length of the measurement light is changed with respect to the optical path length of the reference light.

When the observation of the retinal portion of the fundus is performed as described above and then a mode changing signal from the retinal mode to the choroidal mode is inputted by the mode changing switch 74d, the control unit 70 obtains the tomographic image based on the spectral intensity corrected by the second dispersion correction value.

The control unit 70 moves the reference mirror 31 in the direction such that the inverted image is obtained (the direction such that the reference light is made longer) until the inverted image is obtained. Before moving the reference mirror 31, the control unit 70 regards the detected position of the maximum luminance value in the depth direction of the normal image as the image position P1, and calculates the deviation amount Lg from the depth position S, at which the optical path length of the measurement light and the optical path length of the reference light become equal, to the image position P1. Then, the control unit 70 calculates the movement amount ML of the reference mirror 31 by which the calculated deviation amount Lg becomes zero, and then moves the reference mirror 31 by double the calculated movement amount ML (2ML). Accordingly, the inverted image is obtained.

When the reference mirror 31 is moved to the position at which the inverted image of the fundus tomographic image is obtained as described above and the inverted image is obtained by the interference optical system 200, the control unit 70 displays the inverted image of the fundus tomographic image at a given display position on the monitor 75. When the selection signal of the choroidal mode is inputted, the control unit 70 vertically reverses and displays the extracted first image data G1 on the monitor 75. It is also preferable that the control unit 70 extracts and displays the first image data G1 on the monitor 75 in the retinal mode and extracts and displays the second image data G2 on the monitor 75 in the choroidal mode.

Because the tomographic image obtained here has passed through the correction processing using the second dispersion correction data for the inverted image obtainment, the inverted image of the fundus tomographic image with high contrast and high definition is displayed on the monitor 75. Thus, the examiner is allowed to observe an area of the choroid of the fundus with high visibility.

The determination whether the fundus tomographic image is the normal image or the inverted image is not limited to the technique described above, and may be performed in such a manner that the luminance distribution in the tomographic image when the normal image of the fundus tomographic image is obtained and the luminance distribution in the tomographic image when the inverted image of the fundus tomographic image is obtained are compared and a determination condition which allows for the determination whether the fundus tomographic image is the normal image or the inverted image is established in consideration of a result of the comparison. For example, whether a half width with respect to the maximum luminance value in the depth direction is beyond a given allowable width is used as the determination condition.

In the descriptions provided above, the determination whether the fundus tomographic image is the normal image or the inverted image is performed by using the luminance distribution in the tomographic image. However, it is also preferable that the sectional shape of the tomographic image when the normal image of the fundus tomographic image is obtained and the sectional shape of the tomographic image when the inverted image of the fundus tomographic image is obtained are compared, and a determination condition which allows for the determination whether the fundus tomographic image is the normal image or the inverted image is established in consideration of a result of the comparison. For example, a symmetric property of the normal image and the inverted image in the depth direction is utilized. To be specific, a retinal pigment epithelium portion is extracted from the first image data G1 of the fundus tomographic image (e.g., data of a luminance value exceeding a predetermined threshold value which corresponds to a luminance value of the retinal pigment epithelium portion is extracted) by image processing, and the determination whether the fundus tomographic image is the normal image or the inverted image is performed based on the curved shape of the extracted retinal pigment epithelium portion.

In the descriptions provided above, the fundus photographing apparatus is shown as an example. However, the present invention is not limited thereto and is applicable to an ophthalmic apparatus arranged to photograph a given portion of an examinee's eye. For example, the present invention is applicable to an anterior-segment photographing apparatus arranged to photograph a tomographic image of an anterior-segment of an examinee's eye.

In addition, the present invention is applicable not only to the ophthalmic apparatus but also to an optical tomographic image photographing apparatus arranged to photograph tomographic images of a living body part other than the eye (e.g., a skin and a blood vessel) and a specimen other than living body parts. In such a case, a tomographic image which is high in visibility on the front side of the examined object is identified as a normal image, and a tomographic image which is high invisibility on the back side of the examined object is identified as an inverted image.

The foregoing description of the preferred embodiments of the invention has been presented for purposes of illustration and description. It is not intended to be exhaustive or to limit the invention to the precise form disclosed, and modifications and variations are possible in the light of the above teachings or may be acquired from practice of the invention. The embodiments chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. An optical tomographic photographing apparatus comprising:

an interference optical system arranged to detect spectral information from interference light of measurement light projected onto an examined object and reference light, and comprising an optical scanner arranged to scan the measurement light which is emitted from a light source on the examined object; and a driving unit arranged to change an optical path length by moving an optical member disposed in an optical path of one of the reference light and the measurement light in an optical axis direction;

a monitor;

a control unit arranged to control driving of the driving unit, and to obtain a tomographic image of the examined object by performing Fourier analysis on the spectral information and display the obtained tomographic image on a screen of the monitor; and an image setting unit arranged to previously set the tomographic image which is displayed on the screen of the monitor to be one of a normal image and an inverted image, wherein the control unit is arranged to control the driving of the driving unit so as to move the optical member from an initial position in a predetermined direction and determine presence or absence of the tomographic image on an image obtained at each position, when the presence of the tomographic image is detected, determine whether the tomographic image is the normal image or the inverted image, and when it is determined that the tomographic image is not the image previously set by the image setting unit, move the optical member in a direction such that the previously set image is obtained, and when it is determined that the tomographic image is the image previously set by the image setting unit, move the optical member so that a position of the tomographic image in the depth direction coincides with a predetermined adjustment position and then stop the driving of the driving unit.

2. The optical tomographic photographing apparatus according to claim 1, wherein when the presence of the tomographic image is detected, the control unit determines whether the normal image and the inverted image are coexistent in the tomographic image, and when it is determined that the normal image and the inverted image are coexistent, the control unit moves the optical member in a direction such that only the previously set image is obtained.

3. The optical tomographic photographing apparatus according to claim 1, further comprising:
- mode selecting means arranged to select either of a first mode for observing a front surface side of the examined object and a second mode for observing a back surface side of the examined object, wherein
- the image setting unit is arranged to set, when a selection signal of the first mode is outputted from the mode selecting means, that the normal image is displayed on the screen of the monitor, and
- the setting unit is arranged to set, when a selection signal of the second mode is outputted from the mode selecting means, that the inverted image is displayed on the screen of the monitor.

4. The optical tomographic photographing apparatus according to claim 1, wherein the control unit is arranged to set the initial position to be at a position such that the optical path length is increasable and decreasable.

5. The optical tomographic photographing apparatus according to claim 4, wherein
- the examined object comprises a fundus, and
- the control unit is arranged to move the optical member while setting the initial position to be in the vicinity of a position corresponding to an average eye axial length of a human eye.

* * * * *